(12) United States Patent
Toriya et al.

(10) Patent No.: US 8,189,976 B2
(45) Date of Patent: May 29, 2012

(54) ENDOSCOPE SYSTEM

(75) Inventors: Tomoaki Toriya, Sakura (JP); Takashi Tsumanuma, Sakura (JP); Keiji Kaneda, Sakura (JP); Kenichi Nakatate, Sakura (JP)

(73) Assignee: Fujikura Ltd., Tokyo (JP)

( * ) Notice: Subject to any disclaimer, the term of this patent is extended or adjusted under 35 U.S.C. 154(b) by 208 days.

(21) Appl. No.: 12/539,209

(22) Filed: Aug. 11, 2009

(65) Prior Publication Data
US 2010/0046897 A1 Feb. 25, 2010

(30) Foreign Application Priority Data

Aug. 19, 2008 (JP) ................................ 2008-210942

(51) Int. Cl.
*G02B 6/06* (2006.01)
*G02B 6/036* (2006.01)
(52) U.S. Cl. ........................................ 385/117; 385/126
(58) Field of Classification Search .................. 385/117, 385/115, 116, 119, 123, 141, 126, 127, 128
See application file for complete search history.

(56) References Cited

U.S. PATENT DOCUMENTS

| | | | |
|---|---|---|---|
| 4,615,583 A | 10/1986 | Tsuno et al. | |
| 6,013,025 A | 1/2000 | Bonne et al. | |
| 6,041,154 A * | 3/2000 | Ono et al. | 385/116 |
| 6,663,560 B2 * | 12/2003 | MacAulay et al. | 600/160 |
| 7,235,047 B2 * | 6/2007 | MacAulay et al. | 600/182 |
| 2003/0076571 A1 | 4/2003 | MacAulay et al. | |
| 2004/0147808 A1 * | 7/2004 | MacAulay et al. | 600/160 |
| 2005/0192480 A1 | 9/2005 | Toriya et al. | |
| 2005/0203341 A1 * | 9/2005 | Welker et al. | 600/130 |
| 2005/0277810 A1 | 12/2005 | Irion | |
| 2007/0172180 A1 * | 7/2007 | Pillers et al. | 385/115 |
| 2008/0107386 A1 | 5/2008 | Kudou | |
| 2010/0021114 A1 * | 1/2010 | Chen et al. | 385/116 |
| 2010/0046897 A1 * | 2/2010 | Toriya et al. | 385/117 |

FOREIGN PATENT DOCUMENTS

| | | |
|---|---|---|
| EP | 2374427 A1 | 10/2011 |
| JP | 6-174948 A | 6/1994 |
| JP | 2005-237436 A | 9/2005 |
| JP | 2008-310042 A | 12/2008 |
| WO | 91/15793 A1 | 10/1991 |

OTHER PUBLICATIONS

European Office Action dated Mar. 2, 2012 issued in European Application No. 09251999.0.

\* cited by examiner

*Primary Examiner* — Brian Healy
(74) *Attorney, Agent, or Firm* — Sughrue Mion, PLLC

(57) ABSTRACT

An endoscope system of the present invention includes: an image fiber with an image fiber main body made of a plurality of cores for forming pixels and a cladding common thereto; and an optical system connected to an eyepiece side of the image fiber for causing laser light to enter the image fiber and for taking in an image from the image fiber, in which the image fiber has the cores arranged substantially uniformly over a cross-section of the image fiber main body, the cross-section being perpendicular to a longitudinal direction of the image fiber main body.

6 Claims, 3 Drawing Sheets

ENDOSCOPE SYSTEM

BACKGROUND OF THE INVENTION

1. Field of the Invention

The present invention relates to an endoscope system for use in a medical practice and the like, more particularly to an endoscope system capable of performing image transfer for a finding, diagnosis, or the like of an affected area and also capable of performing laser light transfer for a treatment or the like of the affected area.

Priority is claimed on Japanese Patent Application No. 2008-210942, filed on Aug. 19, 2008, the contents of which are incorporated herein by reference.

2. Description of Related Art

Endoscopes using a fiberscope have been commercialized. In addition, a laser medical treatment method has also been commercialized in which laser light is transmitted to an affected area of the patient through an optical fiber to treat the affected area.

A conventional laser treatment system uses an endoscope for performing an observation and an optical fiber for laser light transmission. The optical fiber is an entity different from the endoscope. In this system, an image of an affected area is firstly checked through the endoscope. Then, based on the image information, an end portion of the optical fiber for laser light transmission is guided to a position suitable for irradiation of laser light onto the affected area, and laser light is irradiated onto this position.

In the system, the positioning accuracy when the end portion of the optical fiber for laser light transmission is directed to the affected area heavily depends on the skill and judgment of a practitioner. This may make it difficult to perform a laser medical treatment.

Therefore, there is proposed an endoscope system with a complex-type optical fiber in which an optical fiber for image transmission and an optical fiber for laser light transmission are combined (for example, see Japanese Unexamined Patent Application, First Publication No. 2005-237436).

FIG. 3 shows a complex-type optical fiber for use in the endoscope system. The complex-type optical fiber 31 has a multitude of optical fibers for image transmission 33 bundled around a large-diameter optical fiber 32 for laser light transmission. These are integrated. The large-diameter optical fiber 32 is made of a core 34 and a cladding 35.

In the endoscope system, the large-diameter optical fiber 32 and the optical fibers for image transmission 33 are integrated. Therefore, it is possible to irradiate laser light correctly onto an affected area without allowing the direction of radiation of the laser light to be out of the observed region.

However, in the above complex-type optical fiber 31, the large-diameter optical fiber 32 that is not involved in image transmission is integrated. Therefore, a blank portion is produced at the center of the image obtained from the optical fibers for image transmission 33.

SUMMARY OF THE INVENTION

The present invention has been achieved in view of the above circumstances, and has an object to provide an endoscope system that is capable of performing both of image observation and laser light irradiation and also produces no blank portion in an obtained image.

(1) An endoscope system of the present invention includes: an image fiber with an image fiber main body made of a plurality of cores for forming pixels and a cladding common thereto; and an optical system connected to an eyepiece side of the image fiber for causing laser light to enter the image fiber and for taking in an image from the image fiber, in which the image fiber has the cores arranged substantially uniformly over a cross-section of the image fiber main body, the cross-section being perpendicular to a longitudinal direction of the image fiber main body.

According to the endoscope system as set forth in the above (1), it is possible to observe a target based on the image obtained from the image fiber.

Furthermore, it is possible to irradiate laser light onto the observed region through the image fiber.

The image fiber has the cores arranged substantially uniformly over the whole cross-section of the image fiber main body. The cross-section is perpendicular to the longitudinal direction of the image fiber main body. Therefore, no blank portion is produced in the image obtained from the image fiber, and the irradiation position of laser light is not limited.

Consequently, it is possible to irradiate laser light onto a necessary position in the range of the image without fail.

As a result, for example, it is possible to find and diagnose an affected area based on the image obtained from the image fiber, and to irradiate laser light onto the affected area, to thereby perform a laser medical treatment.

At this time, no blank portion is produced in the image, and the irradiation position of laser light is not limited. Therefore, it is possible to irradiate laser light onto a necessary position. This heightens an effect of treatment.

(2) In the endoscope system according to the above (1), the optical system may transmit near-infrared light as the laser light to the image fiber.

(3) In the endoscope system according to the above (1), the core may be made from silica glass doped with $GeO_2$.

(4) The endoscope system according to the above (1) may further include a display portion for displaying the image.

DETAILED DESCRIPTION OF THE INVENTION

Hereunder is a description of one embodiment of an endoscope system of the present invention with reference to the drawings.

Figure 1:
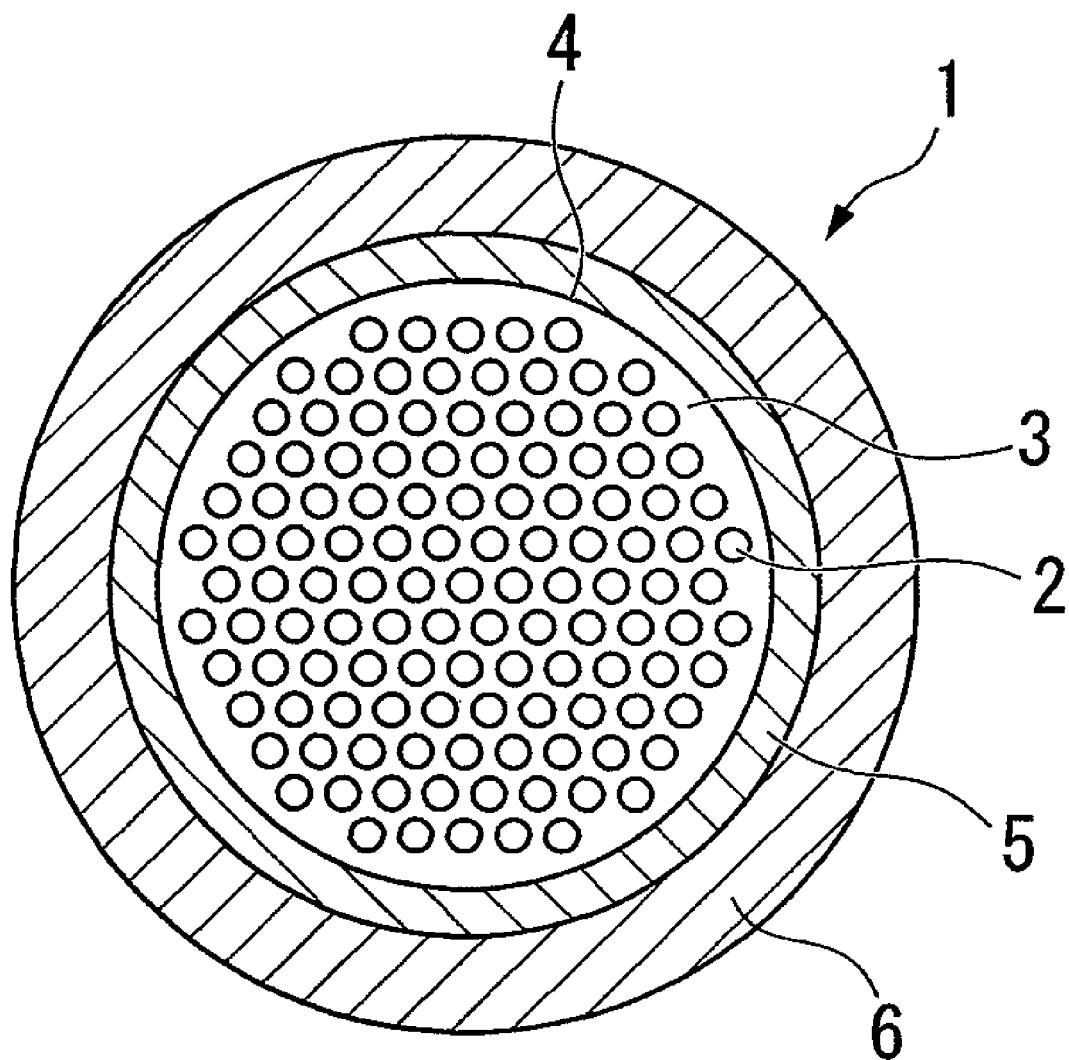
FIG. 1 is a cross-sectional view showing an image fiber for use in one embodiment of an endoscope system of the present invention.
Figure 2:
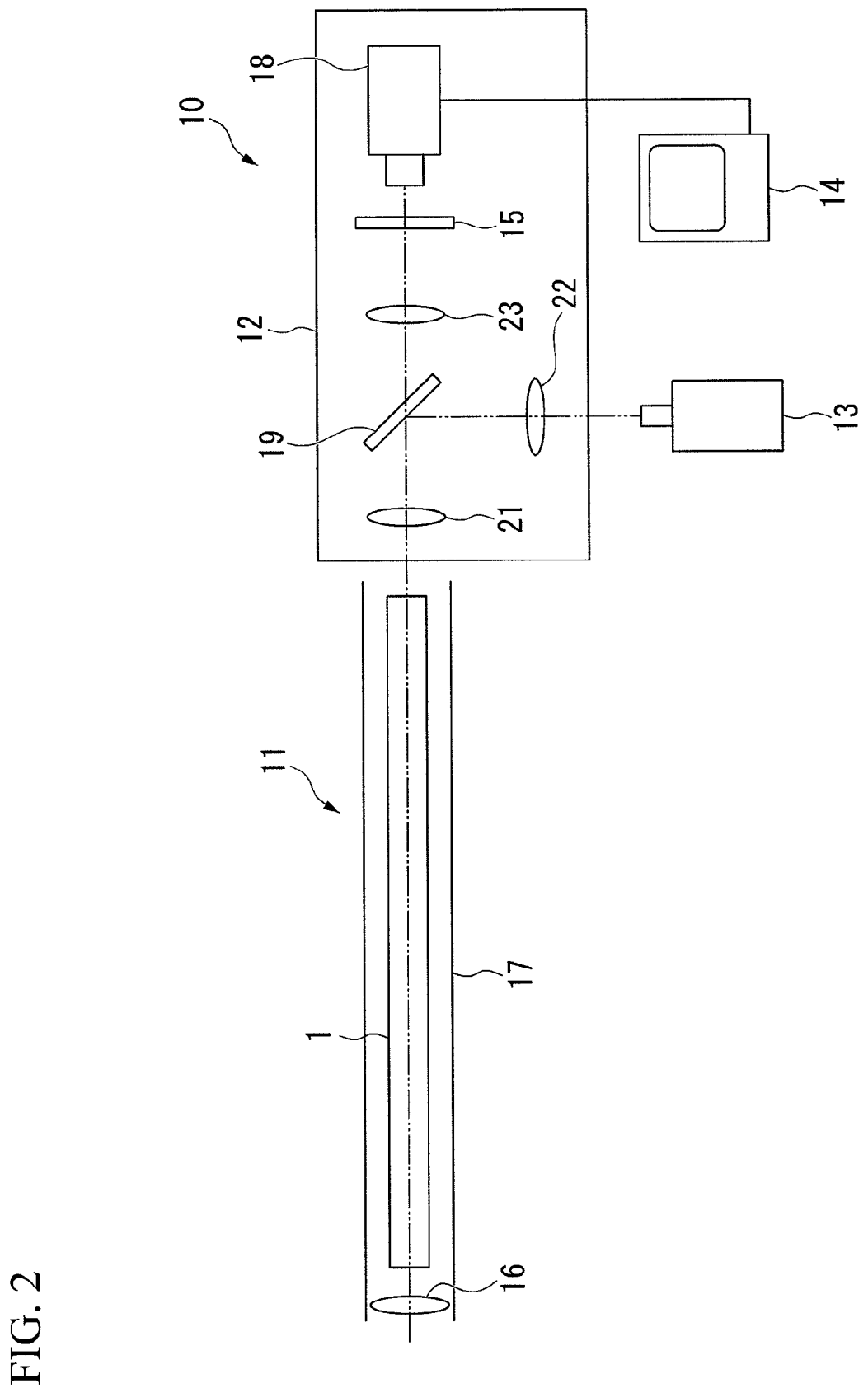
FIG. 2 is a configuration diagram showing one embodiment of an endoscope system of the present invention.
Figure 3:
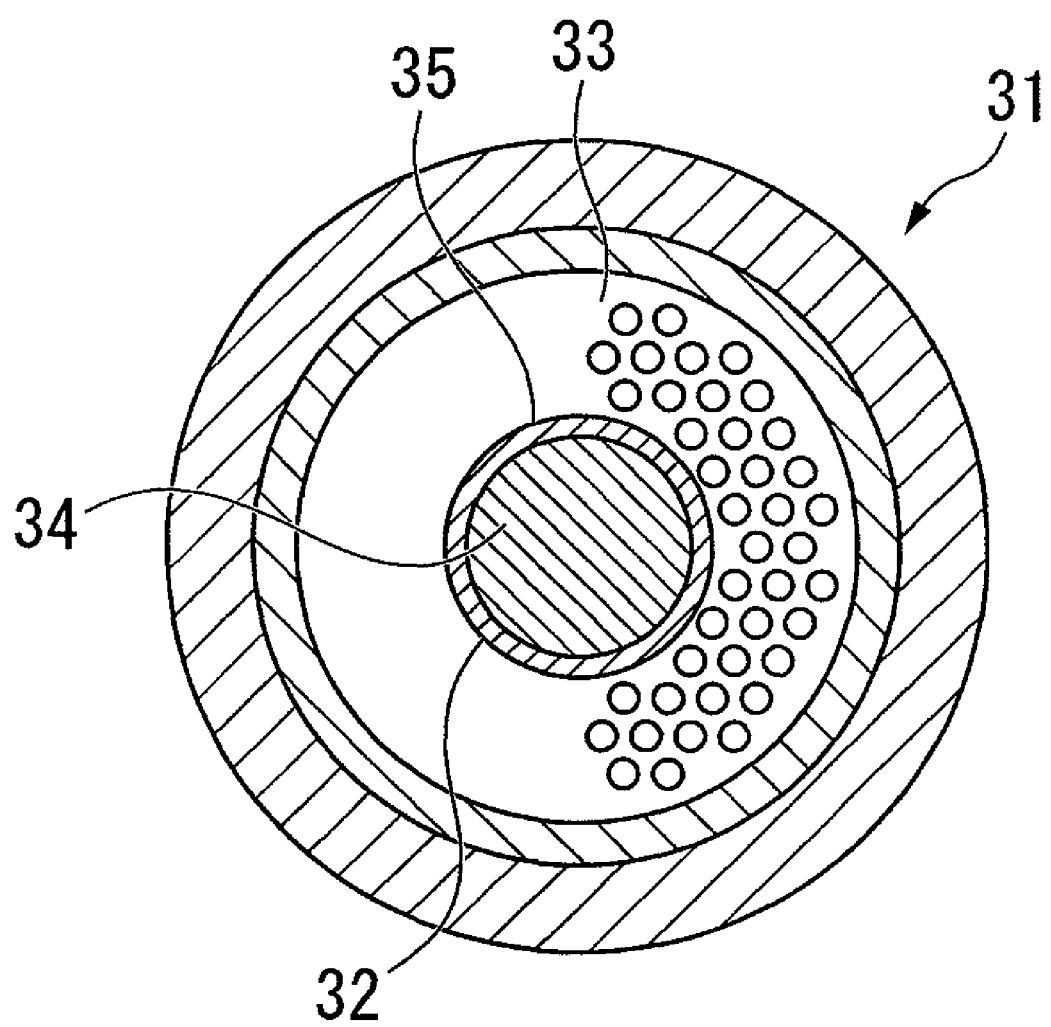
FIG. 3 is a cross-sectional view showing an image fiber (a complex-type optical fiber) for use in one example of a conventional endoscope system.

FIG. 1 is a cross-sectional view showing an image fiber 1 for use in an endoscope system 10, which is one embodiment of the present invention. FIG. 2 is a diagram showing a schematic configuration of the endoscope system 10 according to the embodiment.

As shown in FIG. 2, the endoscope system 10 of the present embodiment includes: a fiberscope 11 provided with an image fiber 1; an optical system 12 connected to an eyepiece side of the fiberscope 11; a laser oscillator 13 (a laser light source) for transmitting laser light (irradiation light) to the optical system 12; and a monitor 14 (a display portion) for displaying an image based on an image signal from the optical system 12.

The fiberscope 11 includes a protection tube 17 in which the image fiber 1 and an objective lens 16 placed on an objective side of the image fiber 1 are provided.

As shown in FIG. 1, the image fiber 1 has an image fiber main body 4 in which a multitude of core-cladding-type silica-based optical fibers are bundled and fused into an integrated entity. The image fiber main body 4 is provided inside a silica jacket layer 5. Around an outer circumference of the silica jacket layer 5, there is provided a resin coating layer 6.

The image fiber main body 4 is a multi-core fiber having a multitude of cores 2 and a common cladding 3 sandwiched between the cores 2. That is, as shown in FIG. 1, the image fiber main body 4 includes: a multitude of cores 2 arranged like islands independent of one another; and a cladding 3 continuously formed around these.

The cores 2 function as pixels of an image obtained by the image fiber 1.

It is preferable that the core 2 be made from silica glass, especially silica glass doped with germanium oxide ($GeO_2$). Doping of $GeO_2$ improves transmission characteristics of near-infrared light (for example, wavelengths of 0.7 to 2.5 μm).

Each of the cores 2 has the same outer diameter (pixel diameter). The outer diameter of the cores 2 may be, for example, 3 to 12 μm. The distance between the cores 2 may be, for example, 1.1 to 2 times the diameter of the core 2.

The cores 2 are arranged substantially uniformly over the whole of the cross-section of the image fiber main body 4. The cross-section is perpendicular to the longitudinal direction of the image fiber main body 4.

"Arranged uniformly" means "arranged over the whole region of the cross-section of the image fiber main body 4 without being distributed unevenly in a part of the region."

The distances between the adjacent cores 2 may be substantially uniform.

The number of pixels N can be found from the following equation (1) where d is a distance between the cores 2 and D is a circle diameter.

$$N=0.9\times(D/d)^2 \quad (1)$$

The circle diameter is a diameter of a range through which light propagates in the cross-section of the image fiber main body 4 (image circle).

It is preferable that the number of cores 2 (the number of pixels) is approximately 1000 to 100000.

The distance between the cores 2 is set based on a refractive index difference between the core 2 and the cladding 3. The refractive index difference can be 2 to 5%, preferably 3.5 to 4% with respect to the core 2. That is, the refractive index of the core 2 is 2 to 5%, and preferably 3.5 to 4% higher than that of the cladding 3.

The cladding 3 is made from pure silica glass or silica-based glass with a refractive index lower than that of pure silica glass. Silica-based glass with a refractive index lower than that of pure silica glass includes one in which silica glass is doped with fluorine (F), boron (B), or the like.

As the image fiber main body 4, a graded-index-type optical fiber may be adopted.

The silica jacket layer 5 is made from, for example, pure silica glass.

The resin coating layer 6 can be formed from a resin such as a silicone resin or a polyimide resin. It is preferable that the resin coating layer 6 have a thickness of approximately 20 to 100 μm.

In the fiberscope 11, a light guide (not shown in the figure) for transmitting illumination light to be irradiated onto a target may be provided along the image fiber 1. The light guide fiber may be an optical fiber made from multicomponent glass fiber, an optical fiber made from silica glass, or the like. The light guide is capable of transmitting light from an illumination light source (not shown in the figure) as illumination light to a target.

The optical system 12 includes: a CCD camera 18 (an image pickup apparatus); a wavelength filter 19 for causing laser light from the laser oscillator 13 to enter the image fiber 1 and also for transmitting light from the image fiber 1 and sending the light to the CCD camera 18; and an absorption filter 15 for cutting reflected laser light.

The CCD camera 18 is configured to send a signal, which has been transmitted from the image fiber 1, to the monitor 14, to thereby make the image observable on the monitor 14. The practitioner is capable of operating the fiberscope 11 while observing the image displayed on the monitor 14.

In FIG. 2, reference numerals 21 to 23 denote lenses.

As the monitor 14, a liquid crystal display apparatus, CRT, or the like can be used.

If near-infrared light is used for the laser light source, a filter that transmits visible light and reflects near-infrared light is used as the wavelength filter 19. Thereby, the wavelength filter 19 reflects laser light (near-infrared light) from the laser oscillator 13 to cause the near-infrared light to enter the image fiber 1. In addition, the wavelength filter 19 transmits light (visible light) from the image fiber 1 to direct the visible light to the CCD camera 18.

If visible light is used for the laser light source, a narrow-band pass filter that reflects only a predetermined wavelength (visible light) of laser light emitted from the laser oscillator 13 and transmits other wavelengths in the visible region is used as the wavelength filter 19. In this case, the visible light with the predetermined wavelength of laser light emitted from the laser oscillator 13 enters the image fiber 1.

Furthermore, the narrow-band pass filter is capable of transmitting light (visible light) from the image fiber 1 to direct it to the CCD camera 18. Use of the narrow-band pass filter does not cause a trouble in image quality of the image.

Thus, the wavelength filter 19 has: a function of selectively sending a predetermined wavelength of light to the image fiber 1, that is, of selecting laser light wavelength; and a function of directing the light from the image fiber 1 to the CCD camera 18.

It is possible to select the laser oscillator 13 in accordance with what to treat or the like. For example, ones that emit laser light with wavelengths from visible region to near-infrared region are usable such as a dye laser, an argon ion laser, a semiconductor laser, a Nd:YAG laser, a Ho:YAG laser and the like. In addition, it is also possible to use an excimer laser such as XeCl, KrF, ArF or the like.

Among these, one that emits near-infrared light as laser light, for example, a Nd:YAG laser (wavelength: 1.06 μm), or a Ho:YAG laser (wavelength: 2.1 μm) is preferable.

Next is a description of how to use the endoscope system 10.

When the end of the image fiber 1 is directed to an observation target, light that has traveled through the image fiber 1, passing through the wavelength filter 19, reaches the CCD camera 18 and forms an image. An image signal having been output from the CCD camera 18 is displayed on the monitor 14. This makes it possible, for example, to find and diagnose an affected area.

As shown in FIG. 1, the image fiber 1 has cores 2 arranged substantially uniformly over the whole cross-section of the image fiber main body 4. Therefore, no blank portion is present in the obtained image. This makes it possible to observe the whole region that corresponds to the cross-section of the image fiber main body 4.

The practitioner is capable of operating the fiberscope 11 while observing the image displayed on the monitor 14 (video monitor).

The laser light emitted from the laser oscillator 13 is transmitted to the optical system 12. It then is reflected by the wavelength filter 19 to enter the image fiber 1. The wavelength filter 19 makes it possible to direct only laser light with a predetermined wavelength to the image fiber 1. The laser light having entered the image fiber 1 is emitted from the end of the image fiber 1. It then passes through the objective lens 16 to be irradiated onto the observation target.

As described above, the image fiber 1 has cores 2 arranged substantially uniformly over the whole cross-section of the image fiber main body 4. Therefore, the position in the image fiber main body 4 through which the laser light propagates is not particularly limited. For example, the laser light may propagate through the central portion of the image fiber main body 4. Alternatively, the laser light may propagate through the vicinity of the periphery of the image fiber main body 4.

Therefore, it is possible to optionally select the irradiation position of laser light for a target in accordance with the position and condition of the affected area. For example, the laser light may be irradiated onto the position corresponding to the central portion of the image fiber main body 4. Alternatively, the laser light may be irradiated onto the position corresponding to the vicinity of the periphery of the image fiber main body 4.

The irradiation position of laser light can be set, for example, with the adjustment of the positions of the wavelength filter 19, the filter 15, the lens 21, and the like for determining the entrance position of the laser light into the image fiber 1. This can reduce irradiation of the laser light onto unnecessary regions (healthy regions), to thereby reduce the load on the patient.

In this manner, it is possible to appropriately change the irradiation position. Therefore, for example, a laser with a wavelength of approximately 3 µm can be irradiated with its entrance position fixed at the center of the image region, to thereby incise an affected area. Subsequently, a Ho:YAG laser with a wavelength of 2.1 µm or the like can be irradiated with its entrance position fixed on the peripheral portion of the above region, to thereby perform a treatment such as hemostasis. Thus, according to the endoscope system of the present invention, it is also possible to appropriately change the wavelength of the laser light in accordance with the conditions of the affected areas, and to irradiate the changed wavelengths of the laser light onto each region. As a result, it is possible to heighten an effect of treatment, and also to perform a variety of treatments with only a single insertion of the endoscope system. This decreases the load on the patient.

This irradiation of laser light can have a medical treatment as its objective. For example, it can be used for angiogenesis, angiorrhaphy, lithotripsy, retinal coagulation, and the like. By use of near-infrared light as laser light, it is possible to heat the affected area.

In the endoscope system 10 of the present embodiment, it is possible to observe the target based on the image obtained from the image fiber 1. Furthermore, it is possible to irradiate laser light onto the observed region through the image fiber 1.

The image fiber 1 has the cores arranged substantially uniformly over the whole cross-section of the image fiber main body 4. Therefore, no blank portion is produced in the obtained image, and the irradiation position of laser light is not limited. Consequently, in the range of the image obtained from the image fiber 1, it is possible to irradiate laser light onto a necessary position without fail.

As a result, if the endoscope system 10 of the present embodiment is used for a medical practice, it is possible, for example, to find and diagnose an affected area based on the image obtained from the image fiber 1, and to irradiate laser light onto the affected area, to thereby perform a laser medical treatment. At this time, no blank portion is produced in the image obtained from the image fiber 1, and the irradiation position of laser light is not limited. Therefore, it is possible to irradiate laser light onto a necessary position. This heightens an effect of treatment.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as limited by the foregoing description and is only limited by the scope of the appended claims.

What is claimed is:

1. An endoscope system, comprising:
   an image fiber with an image fiber main body made of a plurality of cores for forming pixels and a cladding common thereto; and
   an optical system connected to an eyepiece side of the image fiber for causing laser light to enter a part of the image fiber and for taking in an image from the image fiber,
   wherein
   the image fiber has the cores arranged substantially uniformly over the whole cross-section of the image fiber main body, the cross-section being perpendicular to a longitudinal direction of the image fiber main body; and
   the propagation position in the image fiber main body through which the laser light propagates is selectable.

2. The endoscope system according to claim 1, wherein the optical system transmits near-infrared light as the laser light to the image fiber.

3. The endoscope system according to claim 1, wherein the core is made from silica glass doped with $GeO_2$.

4. The endoscope system according to claim 1, further comprising a display portion for displaying the image.

5. The endoscope system according to claim 1, wherein the optical system can set the propagation position with the adjustment of the position of one or more optical elements used therein.

6. The endoscope system according to claim 5, wherein the one or more optical elements for setting the propagation position comprise a wavelength filter, absorption filter and lens.

* * * * *